United States Patent
Chen et al.

(10) Patent No.: US 11,346,778 B1
(45) Date of Patent: May 31, 2022

(54) METHOD FOR DETECTING PETROLEUM WITH A STAGGERED TOROIDAL CHIP

(71) Applicant: UNIVERSITY OF SHANGHAI FOR SCIENCE AND TECHNOLOGY, Shanghai (CN)

(72) Inventors: Lin Chen, Shanghai (CN); Yiming Zhu, Shanghai (CN); Zhengji Ni, Shanghai (CN); Songlin Zhuang, Shanghai (CN)

( * ) Notice: Subject to any disclaimer, the term of this patent is extended or adjusted under 35 U.S.C. 154(b) by 1 day.

(21) Appl. No.: 17/271,570

(22) PCT Filed: Jan. 2, 2020

(86) PCT No.: PCT/CN2020/070089
§ 371 (c)(1),
(2) Date: Feb. 25, 2021

(87) PCT Pub. No.: WO2021/134749
PCT Pub. Date: Jul. 8, 2021

(51) Int. Cl.
*G01N 21/3586* (2014.01)
*G01N 21/25* (2006.01)
*G01N 33/28* (2006.01)

(52) U.S. Cl.
CPC ..... *G01N 21/3586* (2013.01); *G01N 33/2823* (2013.01)

(58) Field of Classification Search
CPC . G01N 21/3586; G01N 33/2823; G01N 21/25
See application file for complete search history.

(56) References Cited

U.S. PATENT DOCUMENTS

| | | | |
|---|---|---|---|
| 2004/0233458 A1* | 11/2004 | Frick | G01D 5/35345 331/65 |
| 2015/0090881 A1* | 4/2015 | King | G01N 21/3586 206/564 |

FOREIGN PATENT DOCUMENTS

| | | | |
|---|---|---|---|
| CN | 102621083 A | | 8/2012 |
| CN | 104215603 A | * | 12/2014 |

(Continued)

OTHER PUBLICATIONS

Ma, Xin, International search report and written opinion by CNIPA as the International search authority, dated Sep. 27, 2020.

(Continued)

*Primary Examiner* — David P Porta
*Assistant Examiner* — Fani Polyzos Boosalis
(74) *Attorney, Agent, or Firm* — OPES IP Consulting Co. Ltd.

(57) ABSTRACT

The present invention provides a method for detecting petroleum with a staggered toroidal chip, comprising the following steps: step 1, dry the test environment of a terahertz spectrum analysis system, measure a spectrum under dry conditions, and use the spectrum as a reference spectrum; step 2, use a pipette to transfer a crude oil sample and evenly smear it on the metasurface of a staggered toroidal chip; step 3, put the staggered toroidal chip coated with the crude oil sample into the dried terahertz spectrum analysis system, let a terahertz pulse signal of the terahertz spectrum analysis system to be vertically irradiated on the chip for detection, and then get a detection spectrum of the crude oil sample; step 4, subtract the reference spectrum from the detection spectrum, and then get a transmission spectrum of the crude oil sample, wherein the staggered toroidal chip is a terahertz chip designed based on the dual-torus toroidal effect.

6 Claims, 4 Drawing Sheets

(56) References Cited

FOREIGN PATENT DOCUMENTS

| | | | | | |
|---|---|---|---|---|---|
| CN | 104215603 | A | | 12/2014 | |
| CN | 105445219 | A | * | 3/2016 | .............. G01N 1/36 |
| CN | 105445219 | A | | 3/2016 | |
| CN | 108414473 | A | | 8/2018 | |
| CN | 108627466 | A | | 10/2018 | |
| CN | 109557050 | A | | 4/2019 | |
| CN | 109580443 | A | | 4/2019 | |
| CN | 109580535 | A | | 4/2019 | |
| JP | 2013064646 | A | | 4/2013 | |

OTHER PUBLICATIONS

Liang, Li et al., "Research progress of terahertz sensor based on artificial microstructure", Infrared and Laser Engineering, p. 12-28, vol. 48, No. 2, Feb. 28, 2019.

* cited by examiner (A)

(B)

(C)

(D)

METHOD FOR DETECTING PETROLEUM WITH A STAGGERED TOROIDAL CHIP

CROSS REFERENCE TO RELATED APPLICATIONS

This application claims priority to PCT Application No. PCT/CN2020/070089 filed on Jan. 2, 2020, the content of which is incorporated herein in its entirety by reference.

FIELD OF THE INVENTION

The present invention belongs to material detection field of terahertz toroidal chip, especially relates to a method for detecting petroleum with a staggered toroidal chip.

BACKGROUND OF THE INVENTION

Since the 1990s, people started the journey of using the traditional time-domain terahertz spectrum analysis system to detect substances: using characteristics of terahertz spectrum to detect samples. Studies have shown that although the far-infrared absorption characteristics of some substance are very sensitive to the structure and spatial arrangement of the substance, and terahertz time-domain spectrum technology can identify compounds with small differences in sample. However, the traditional sample detection method using time-domain terahertz spectrum system requires a large number of samples, has low accuracy, needs large experimental equipment. Besides, there are problems such as weak radiant power of terahertz sources and large absorption of polar molecular samples. What is more serious is that when testing some materials without absorption peaks in this frequency band, only the dielectric coefficient and absorption coefficient of the material can be measured, which causes great inaccuracy of measurement. These will lead to many difficulties in real-time monitoring applications.

At the beginning of this century, people started to use the terahertz plasmonic enhanced resonance effect (such as Fano resonance) to achieve high-sensitivity microbiological detection. This method solves the limitations of the ordinary terahertz detection, such as the volume of sample is large, the intensity of absorption spectrum is unstable, weak radiation power leads to low signal-to-noise ratio. Surface plasmons can cause an abnormal transmission phenomenon, and the transmission peak corresponding to the abnormal transmission phenomenon usually appears as an asymmetrical line type, called Fano line type. For the Fano resonance caused by the introduction of asymmetry in the metal film metasurface, the non-resonant channel corresponds to the dipole oscillation generated by the interaction of the incident light and the bright state mode, and the resonance channel is related to the dark state generated by the surface plasmon. Fano resonance can enhance the nearby spectral selectivity of the electromagnetic field, and produce narrow-band spectral characteristics, which greatly enhances the interaction of light with materials close to (or in direct contact with) the surface. Therefore, even weak disturbances in the plasma electromagnetic environment can significantly change its scattering characteristics. For absorbing media, field enhancement can lead to a broadening and reduction of the amplitude of the Rayleigh characteristic associated with Fano resonance. But its disadvantage is that in addition to drifting with the reaction process, Fano resonance is distorted, which is caused by the asymmetry of the Fano oscillation, and the Fano oscillation itself is unstable with the long detection time. Therefore, based on the above-mentioned Fano resonance, it is necessary to further find a more stable resonance mode, which has become a key problem to be solved urgently for such high-Q microcavity chips.

SUMMARY OF THE INVENTION

Targeting at the problems above, the present invention provides a method for detecting petroleum with a staggered toroidal chip.

The present invention provides a method for detecting petroleum with a staggered toroidal chip, comprising the following steps: step 1, dry the test environment of the terahertz spectrum analysis system, measure the spectrum under dry conditions, and use the spectrum as a reference spectrum; step 2, use a pipette to transfer the crude oil sample and evenly smear it on the metasurface of a staggered toroidal chip; step 3, put the staggered toroidal chip coated with the crude oil sample into the dried terahertz spectrum analysis system, let the terahertz pulse signal of the terahertz spectrum analysis system to be vertically irradiated on the chip for detection, and then get a detection spectrum of the crude oil sample; step 4, subtract the reference spectrum from the detection spectrum, and then get a transmission spectrum of the crude oil sample, wherein, the staggered toroidal chip is a terahertz chip designed based on the dual-torus toroidal effect.

In the above method for detecting petroleum with a staggered toroidal chip, the metasurface of the staggered toroidal chip is a staggered structure, which is composed of two circular split ring resonators, and both the circular split ring resonators have a certain overlapping area, the center of one circular split ring resonator is on the left of symmetry axis of staggered toroidal chip, and the gap is on the right of the left center, the center of the other circular split resonator is on the right of symmetry axis of the staggered toroidal chip, and the gap is on the left of the right center.

In the above method for detecting petroleum with a staggered toroidal chip, the inner radius of the circular split ring resonator is 35 µm, and the outer radius is 40 µm, the size of the gap is 4 µm.

In the above method for detecting petroleum with a staggered toroidal chip, the terahertz spectrum analysis system is Advantest 7400 system, and its detection method is transmission detection.

In the above method for detecting petroleum with a staggered toroidal chip, the volume of the crude oil sample is 1 µL~10 µL, the thickness of the crude oil sample smeared on the staggered toroidal chip is 1 µm~µm.

In the above method for detecting petroleum with a staggered toroidal chip, the volume of the crude oil sample is 2 µL, the thickness of the crude oil sample smeared on the staggered toroidal chip is 1 µm.

Function and Effect of the Invention

By the method for detecting petroleum with a staggered toroidal chip in the present invention, the spectral detection of crude oil samples can be realized, because the method uses a staggered toroidal chip and combines the terahertz time-domain spectroscopy detection technology. Moreover, because the staggered toroidal chip is a terahertz chip designed based on the dual-torus toroidal effect, and it can effectively improve the unstable spectrum caused by general metamaterial excitation such as Fano resonance, so the detection of this method is better.

In addition, the staggered toroidal chip in the present invention has a small volume and can greatly improve the portability of detection.

In addition, the petroleum detection through the method of the present invention, requires less samples and short time, and can realize rapid, accurate, trace and real-time spectroscopic detection.

DETAILED DESCRIPTION OF THE INVENTION

An embodiment of the present utility model will be described in detail herein below with reference to the figures.

Embodiment 1

This embodiment provides a method for detecting petroleum with a staggered toroidal chip, comprising the following steps:

Step 1, dry the test environment of a terahertz spectrum analysis system to eliminate the influence of air water molecules on the experiment, measure a spectrum under dry conditions, and use this spectrum as a reference spectrum.

Wherein, the terahertz spectrum analysis system is Advantest 7400 system, and its detection method is transmission detection. In step 1, the process of dry pretreatment is: before the experiment, remove the water vapor inside the system through the dry air filter unit, and use a hygrometer to monitor the humidity inside the system in real time until the humidity is below 3%.

Step 2, take a 1 cm×1 cm staggered toroidal chip, and then use a pipette to transfer 1 μL~10 μL crude oil sample and evenly smear the crude oil sample on one side of the metasurface of the staggered toroidal chip. The thickness of the crude oil sample smeared on the staggered toroidal chip is 1 μm~3 μm and the thickness of the crude oil sample is as small as possible to facilitate the transmission of the terahertz pulse signal.

The staggered toroidal chip used in the embodiment is a terahertz chip designed based on the dual-torus toroidal effect. Toroidal effect refers to the resonance response caused by current flowing along the center line on a doughnut-like torus, that is, the magnetic dipoles connect end to end to form a vortex distribution. Its advantage is that it breaks the inversion symmetry of space and time at the same time, and has many interesting characteristics, such as magnetoelectric effect, dichroism and non-reciprocal refraction. Its unique current distribution and vortex field distribution can usually achieve strong near-field localization. In addition, utilizing the unique electromagnetic characteristics of dual-torus toroidal, instead of one-torus toroidal, such as high Q value, sensitivity to environment, we have designed the staggered toroidal chip in this embodiment, which is a sensor component with higher sensitivity and stability.

Figure 1:
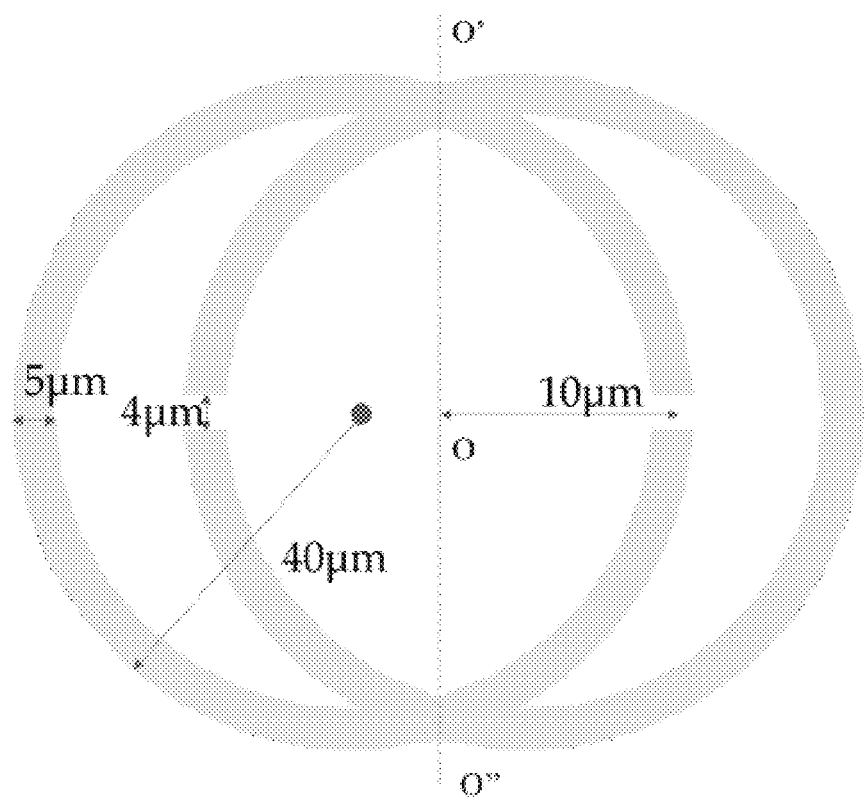
FIG. 1 is a structural illustration of the metasurface of the staggered toroidal chip in embodiment 1.
Figure 2:
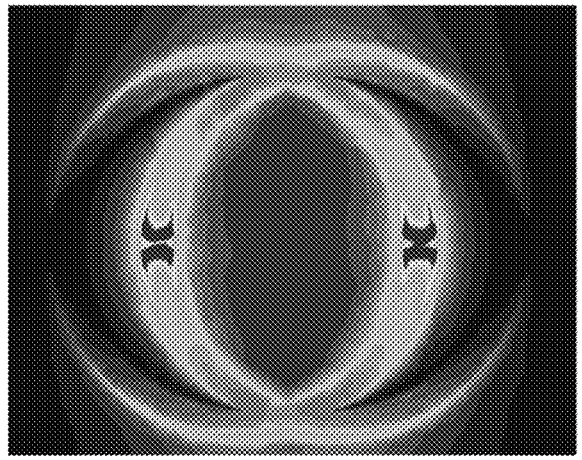
FIG. 2 is a field distribution illustration of dual-torus toroidal effect of the staggered toroidal chip in embodiment 1.
Figure 2:
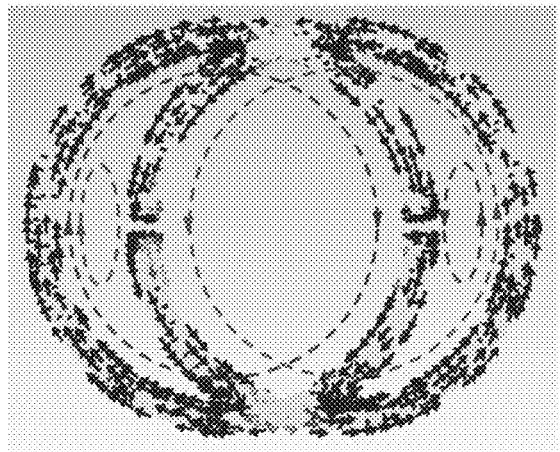
Figure 2:
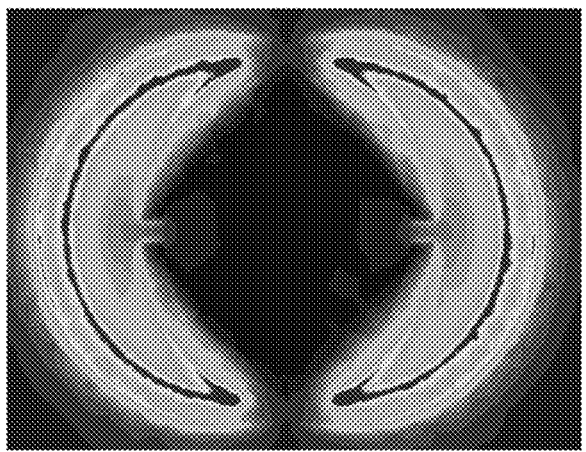
Figure 2:
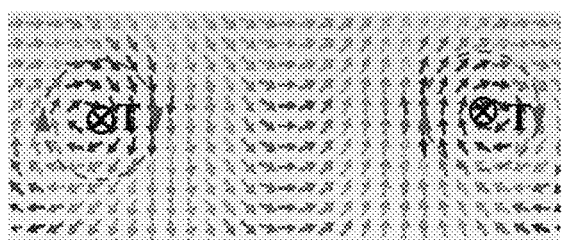

FIG. 1 is a structural illustration of the metasurface of the staggered toroidal chip in embodiment 1. FIG. 2 is a field distribution illustration of dual-torus toroidal effect of the staggered toroidal chip in embodiment 1.

As shown in FIG. 1, the metasurface of the staggered toroidal chip in this embodiment, is a staggered structure, which is composed of two circular split ring resonators, and both the circular split ring resonators have an overlapping area. Wherein, the center of one circular split ring resonator is on the left of symmetry axis (OO') of staggered toroidal chip, and the gap is on the right of the left center; the center of the other circular split ring resonator is on the right of symmetry axis (OO') of staggered toroidal chip, and the gap is on the left of the right center. The inner radius of the circular split ring resonator is 35 μm, and the outer radius is 40 μm, the size of the gap is 4 μm.

As shown in FIG. 2, FIG. 2(A) shows the electromagnetic intensity; FIG. 2(B) shows the surface current distribution; FIG. 2(C) shows the magnetic field strength; FIG. 2(D) shows the vector form of magnetic field with dual-torus. FIG. 2 (A)~FIG. 2 (D) show the surface electric field distribution, surface current distribution, magnetic field distribution and vector distribution of the magnetic field cross section of the metasurface of the staggered toroidal chip near the frequency point 0.546 THz, respectively. Wherein, FIG. 2 (A) shows energy accumulation caused by current shock at the opening; in FIG. 2 (B), the clockwise circle on the left and the counterclockwise ellipse on the right form the reverse current, while the counterclockwise circle on the right and the clockwise ellipse on the left form the reverse current; FIG. 2 (D) shows the circular magnetic dipole moment in FIG. 2 (B) in the dual-torus with perpendicular to the plane generated by the corresponding reverse current at the corresponding left opening and the right opening.

Step 3, put the staggered toroidal chip coated with the crude oil sample into the dried terahertz spectrum analysis system, let a terahertz pulse signal of the terahertz spectrum analysis system to be vertically irradiated on the chip for detection, then perform the procedure of the terahertz spectrum analysis system and detect it for about 5 min, and finally get a detection spectrum of the crude oil sample.

Figure 3:
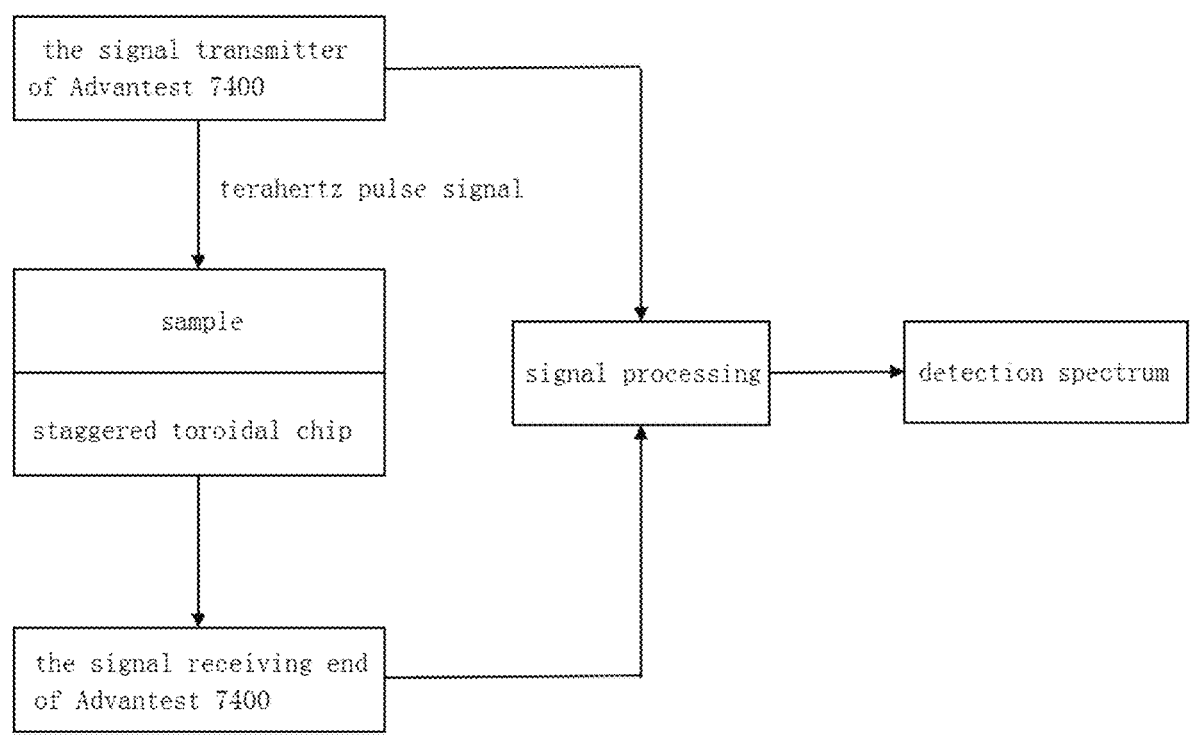
FIG. 3 is a schematic illustration of the detection process of the terahertz spectrum analysis system in embodiment 1.

FIG. 3 is a schematic illustration of the detection process of the terahertz spectrum analysis system in embodiment 1.

As shown in FIG. 3, in step 3, the specific detection process in the Terahertz spectrum analysis system includes: the signal transmitter of the terahertz spectral analysis system (Advantest 7400) emits a terahertz pulse signal, and this terahertz pulse signal is vertically illuminated on the staggered toroidal chip coated with the crude oil sample; then, the signal receiving end of the terahertz spectral analysis system (Advantest 7400) receives the transmitted pulse signal and processes the signal to obtain the detection spectrum.

Step 4, subtract the reference spectrum from the detection spectrum, and then get a transmission spectrum of the crude oil sample, wherein the staggered toroidal chip is a terahertz chip designed based on the dual-torus toroidal effect.

Embodiment 2

In this embodiment, the method for detecting petroleum with a staggered toroidal chip in embodiment 1 is used to detect four crude oil samples from different sources.

The specific testing process of embodiment 2 is as follows:

Step 1, dry the test environment of Advantest 7400 system to eliminate the influence of air water molecules on the experiment, measure a spectrum under dry conditions, and use this spectrum as a reference spectrum.

Step 2, take a 1 cm×1 cm staggered toroidal chip, and then use a pipette to transfer 2 μL crude oil sample and evenly smear the crude oil sample on one side of the metasurface of the staggered toroidal chip. The thickness of the crude oil sample smeared on the staggered toroidal chip is 1 μm.

Step 3, put the staggered toroidal chip coated with the crude oil sample into the dried terahertz spectrum analysis system, let a terahertz pulse signal of the terahertz spectrum analysis system to be vertically irradiated on the chip for detection, then perform the procedure of the terahertz spectrum analysis system and detect it for about 5 min, and finally get a detection spectrum of the crude oil sample.

Step 4, subtract the reference spectrum from the detection spectrum, and then get a transmission spectrum of the crude oil sample, wherein the staggered toroidal chip is a terahertz chip designed based on the dual-torus toroidal effect.

Step 5, repeat steps 2~4 to test the other three crude oil samples. In order to ensure the accuracy of measurement, each time a different sample is tested, a new staggered toroidal chip needs to be replaced.

Figure 4:
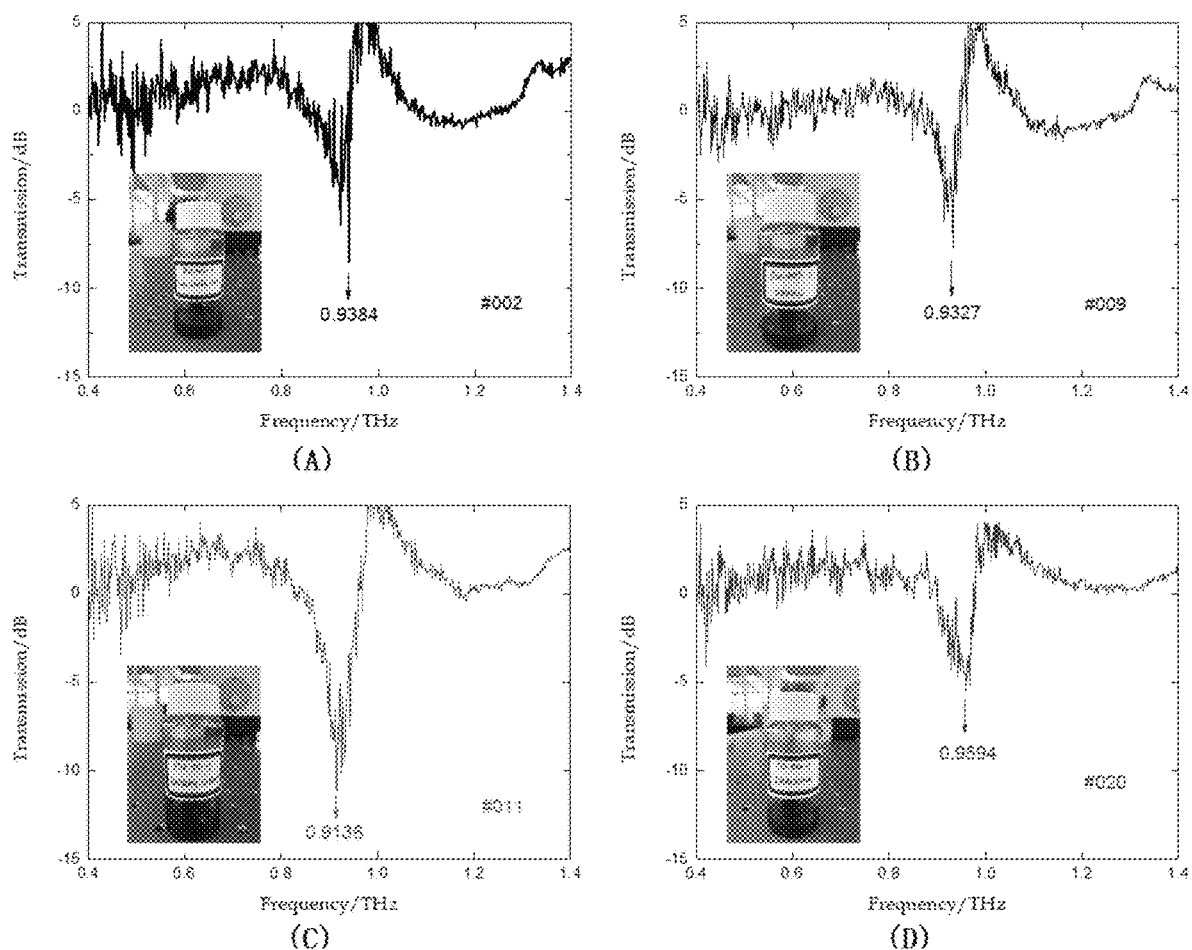
FIG. 4 is a transmission spectrum of four crude oils from different producing areas in embodiment 2.

FIG. 4 is a transmission spectrum of four crude oils from different producing areas in embodiment 2.

As shown in FIG. 4, FIG. 4(A)~FIG. 4(D) respectively show one of four crude oil samples from different origins. The abscissa in the figure represents frequency, and the ordinate represents the transmittance (dB). It can be seen from FIG. 4 that the transmission spectra of the four crude oil samples from different producing areas all show obvious toroidal oscillations, indicating that the measured spectra of the detection method in Example 1 is stable; in addition, the resonance frequencies of the four crude oil samples were slightly different, 0.9384 THz, 0.9327 THz, 0.9136 THz and 0.9594 THz, respectively. And this shows that although the differences in the resonance frequencies of the four crude oil samples are small, the four crude oil samples can still be distinguished by the detection method of embodiment 1, which further indicates the high sensitivity of the detection method of embodiment 1.

Function and Effect of the Embodiments

By the method for detecting petroleum with a staggered toroidal chip in embodiment 1, the spectral detection of crude oil samples can be realized, because the method uses a staggered toroidal chip and combines the terahertz time-domain spectroscopy detection technology. Moreover, because the staggered toroidal chip is a terahertz chip designed based on the dual-torus toroidal effect, and it can effectively improve the unstable spectrum caused by general metamaterial excitation such as Fano resonance, so the detection of this method is better.

In addition, the staggered toroidal chip in embodiment 1 has a small volume and can greatly improve the portability of detection.

In addition, the petroleum detection through the method of embodiment 1, requires less samples and short time, and can realize rapid, accurate, trace and real-time spectroscopic detection.

In addition, the terahertz spectrum analysis system in embodiment 1 is Advantest 7400 system, with a spectral resolution of up to 2.1 GHz, which can realize high-precision material detection in a wide spectral range.

In addition, the test of embodiment 2 shows that the crude oil sample can be more accurately detected by the method of embodiment 1, and the measured spectrum is very stable, so that the crude oil from different sources can be effectively distinguished.

The above embodiments are preferred examples of the invention and are not intended to limit the scope of protection of the invention.

What is claimed is:

1. A method for detecting petroleum with a staggered toroidal chip, comprising the following steps:
    step 1, dry the test environment of a terahertz spectrum analysis system, measure a spectrum under dry conditions, and use the spectrum as a reference spectrum;
    step 2, use a pipette to transfer a crude oil sample and evenly smear it on the metasurface of a staggered toroidal chip;
    step 3, put said staggered toroidal chip coated with said crude oil sample into the dried terahertz spectrum analysis system, let a terahertz pulse signal of said terahertz spectrum analysis system to be vertically irradiated on the chip for detection, and then get a detection spectrum of said crude oil sample;
    step 4, subtract said reference spectrum from said detection spectrum, and then get a transmission spectrum of said crude oil sample;
    wherein said staggered toroidal chip is a terahertz chip designed based on the dual-torus toroidal effect.

2. The method for detecting petroleum with a staggered toroidal chip according to claim 1,
    wherein said metasurface of said staggered toroidal chip is a staggered structure, which is composed of two circular split ring resonators, and both said circular split ring resonators have a certain overlapping area,
    the center of one said circular split ring resonator is on the left of symmetry axis of said staggered toroidal chip, and the gap is on the right of the left center,
    the center of the other circular split resonator is on the right of symmetry axis of said staggered toroidal chip, and the gap is on the left of the right center.

3. The method for detecting petroleum with a staggered toroidal chip according to claim 2,
    wherein the inner radius of said circular split ring resonator is 35 μm, and the outer radius is 40 μm, the size of said gap is 4 μm.

4. The method for detecting petroleum with a staggered toroidal chip according to claim 1,
    wherein said terahertz spectrum analysis system is Advantest 7400 system, and its detection method is transmission detection.

5. The method for detecting petroleum with a staggered toroidal chip according to claim 1,
    wherein the volume of said crude oil sample is 1 μL~10 μL, the thickness of said crude oil sample smeared on said staggered toroidal chip is 1 μm~3 μm.

6. The method for detecting petroleum with a staggered toroidal chip according to claim 5,
    wherein the volume of said crude oil sample is 2 μL, the thickness of said crude oil sample smeared on said staggered toroidal chip is 1 μm.

* * * * *